(12) United States Patent
Boffa

(10) Patent No.: US 9,018,148 B2
(45) Date of Patent: Apr. 28, 2015

(54) METHOD AND SYSTEM FOR SCREENING LUBRICATING OIL COMPOSITIONS

(75) Inventor: Alexander B Boffa, Richmond, CA (US)

(73) Assignee: Cherron Oronite Company LLC, San Ramon, CA (US)

( * ) Notice: Subject to any disclaimer, the term of this patent is extended or adjusted under 35 U.S.C. 154(b) by 1615 days.

(21) Appl. No.: 11/116,531

(22) Filed: Apr. 28, 2005

(65) Prior Publication Data

US 2006/0247137 A1    Nov. 2, 2006

(51) Int. Cl.
| | | |
|---|---|---|
| G01N 33/26 | (2006.01) | |
| G06Q 10/00 | (2012.01) | |
| C10M 169/04 | (2006.01) | |
| G06Q 10/04 | (2012.01) | |

(52) U.S. Cl.
CPC ........ G06Q 10/04 (2013.01); G01N 2291/0226 (2013.01)

(58) Field of Classification Search
USPC ........................................................ 508/110
See application file for complete search history.

(56) References Cited

U.S. PATENT DOCUMENTS

| | | | |
|---|---|---|---|
| 5,699,270 A | 12/1997 | Ashe et al. | |
| 5,796,251 A | 8/1998 | Le Febre et al. | |
| 5,892,507 A * | 4/1999 | Moorby et al. | ............... 715/205 |
| 6,317,654 B1 | 11/2001 | Gleeson et al. | |

FOREIGN PATENT DOCUMENTS

| | | |
|---|---|---|
| EP | 0706050 | 10/1994 |
| EP | 1102187 | 11/2000 |
| WO | WO 01/80119 | 10/2001 |
| WO | WO 2005/044961 | 5/2005 |
| WO | WO 2005/045627 | 5/2005 |
| WO | WO 2005/079277 | 9/2005 |
| WO | WO 2005/095952 | 10/2005 |

OTHER PUBLICATIONS

Konno, et al. "The development of computational chemistry approach to predict the viscosity of lubricants", Tribology International 36 (2003) 455-458.

Manuel R. Conde, "Estimation of Thermophysical Properties of Lubricating Oils and their Solutions with Refrigerants: An Appraisal of Existing Methods", Applied Thermal Engineering, vol. 16, No. 1, pp. 51-61 (1996).

* cited by examiner

*Primary Examiner* — Jim Goloboy

(57) ABSTRACT

A method for screening a lubricating oil composition having at least one base oil of lubricating viscosity and at least one lubricating oil additive is provided, the method comprising the steps of (a) inputting into a computational device an amount of each of the at least one lubricating oil additive, based on the total weight of the lubricating oil composition and, optionally, a value of at least one property associated with each of the at least one base oil of lubricating viscosity; (b) computing a prediction of at least one lubricating oil composition property-determining test result for the lubricating oil composition; (c) computing a cost for the lubricating oil composition; and (d) outputting the results. Also provided are systems and computer program devices for screening lubricating oil compositions.

16 Claims, 7 Drawing Sheets

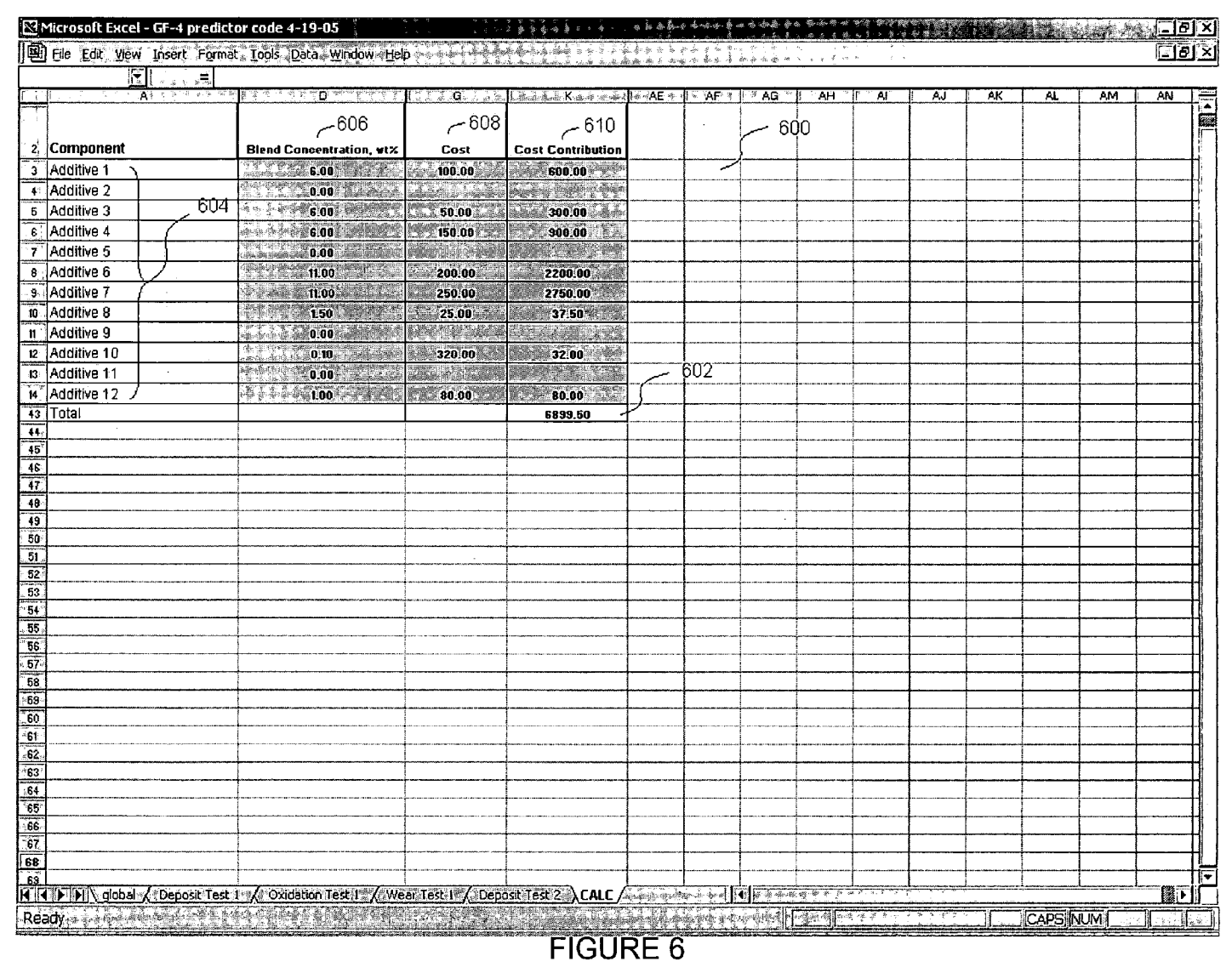

| Component | Blend Concentration, wt% | Cost | Cost Contribution |
|---|---|---|---|
| Additive 1 | 6.00 | 100.00 | 600.00 |
| Additive 2 | 0.00 | | |
| Additive 3 | 6.00 | 50.00 | 300.00 |
| Additive 4 | 6.00 | 150.00 | 900.00 |
| Additive 5 | 0.00 | | |
| Additive 6 | 11.00 | 200.00 | 2200.00 |
| Additive 7 | 11.00 | 250.00 | 2750.00 |
| Additive 8 | 1.50 | 25.00 | 37.50 |
| Additive 9 | 0.00 | | |
| Additive 10 | 0.10 | 320.00 | 32.00 |
| Additive 11 | 0.00 | | |
| Additive 12 | 1.00 | 80.00 | 80.00 |
| Total | | | 6899.50 |

FIGURE 6

METHOD AND SYSTEM FOR SCREENING LUBRICATING OIL COMPOSITIONS

BACKGROUND OF THE INVENTION

1. Technical Field

The present invention relates generally to a method and system for screening lubricating oil compositions.

2. Description of the Related Art

Formulation development of lubricating oil compositions can be difficult and time consuming due to the complexity of the formulation mixtures as well as the often competing performance properties of the lubricating oil additives used in the compositions. For example, in order to meet specifications of the United States Military Standards MIL-L-46152E and the International Lubricants Standardization and Approval Committee (ILSAC) Standards defined by the Japanese and United States Automobile Industry Association, multiple competing test requirements need to be satisfied. As such, many different tests need to be carried out. Conventionally, these tests are carried out using different test apparatuses, are time-consuming, and are relatively expensive, particularly when applied to the hundreds of samples which may be required to be analyzed.

Presently, research in the lubricant industry involves individually forming candidate lubricating oil compositions and then performing a macro-scale analysis of the candidate compositions by employing a large amount of the candidate to be tested. Additionally, the methods employed for testing each candidate composition require manual operation. This, in turn, significantly reduces the number of compositions that can be tested and identified as leading lubricating oil compositions. Accordingly, existing approaches rely on the experience and intuition of the formulator to provide recommendations for new formulations.

It would therefore be desirable to provide a method and system to rapidly identify leading lubricating oil compositions which meet, for example, industry specifications, customer specifications, etc., while also predicting the cost involved in making such compositions. Additionally, it would be desirable to carry out fewer manual tests on each of the compositions. In this manner, the preparation and screening of a vast number of diverse compositions can be achieved in a more expeditious and inexpensive manner.

SUMMARY OF THE INVENTION

It is therefore a feature of the present invention to provide a method and system for simplifying formulation development of lubricating oil compositions.

It is a further feature of the present invention to vastly increase the information on which formulations are based by computerizing the analysis of information required for such formulations.

Accordingly, in one embodiment of the present invention a computerized method for screening a lubricating oil composition having at least one base oil of lubricating viscosity and at least one lubricating oil additive is provided, the method comprising (a) inputting into a computational device an amount of each of the at least one lubricating oil additive, based on the total weight of the lubricating oil composition and, optionally, a value of at least one property associated with each of the at least one base oil of lubricating viscosity; (b) computing a prediction of at least one lubricating oil composition property-determining test result for the lubricating oil composition; (c) computing a cost for the lubricating oil composition; and (d) outputting the results.

In accordance with a second embodiment of the present invention, a computer system for screening a lubricating oil composition having at least one base oil of lubricating viscosity and at least one lubricating oil additive is provided, the system comprising (a) means for inputting a desired type and amount of each of the at least one lubricating oil additive, based on the total weight of the lubricating oil composition and, optionally, a value of at least one property associated with each of the at least one base oil of lubricating viscosity; (b) means for computing a prediction of at least one lubricating oil composition property-determining test result for the lubricating oil composition; and (c) means for computing a cost for the lubricating oil composition.

In accordance with a third embodiment of the present invention, a computer program device readable by a machine, tangibly embodying a program of instructions executable by the machine to perform method steps for screening a lubricating oil composition having at least one base oil of lubricating viscosity and at least one lubricating oil additive is provided, the method steps comprising (a) inputting into a computational device an amount of each of the at least one lubricating oil additive, based on the total weight of the lubricating oil composition and, optionally, a value of at least one property associated with each of the at least one base oil of lubricating viscosity; (b) computing a prediction of at least one lubricating oil composition property-determining test result for the lubricating oil composition; and (c) computing a cost for the lubricating oil composition.

BRIEF DESCRIPTION OF THE DRAWINGS

Various embodiments are described below with reference to the drawings, in which:

FIG. 6 is a screen shot of a Microsoft Excel worksheet showing an exemplary cost calculation model for the lubricating oil additives employed in the hypothetical lubricating oil composition of FIG. 1.

DETAILED DESCRIPTION OF THE PREFERRED EMBODIMENT(S)

The present invention is directed to a system and method for screening a lubricating oil composition comprising at least one base oil of lubricating viscosity and at least one lubricating oil additive by predicting at least one lubricating oil composition property-determining test result for the composition while also being able to calculate its cost. Accordingly, the amount of manual effort used in preparing and testing such lubricating oil compositions is substantially reduced and is replaced by rapid, effective and reliable test predictions and cost calculations thereby resulting in a vast number of diverse compositions that can be timely evaluated and characterized to identify leading lubricating oil compositions.

Figure 1:
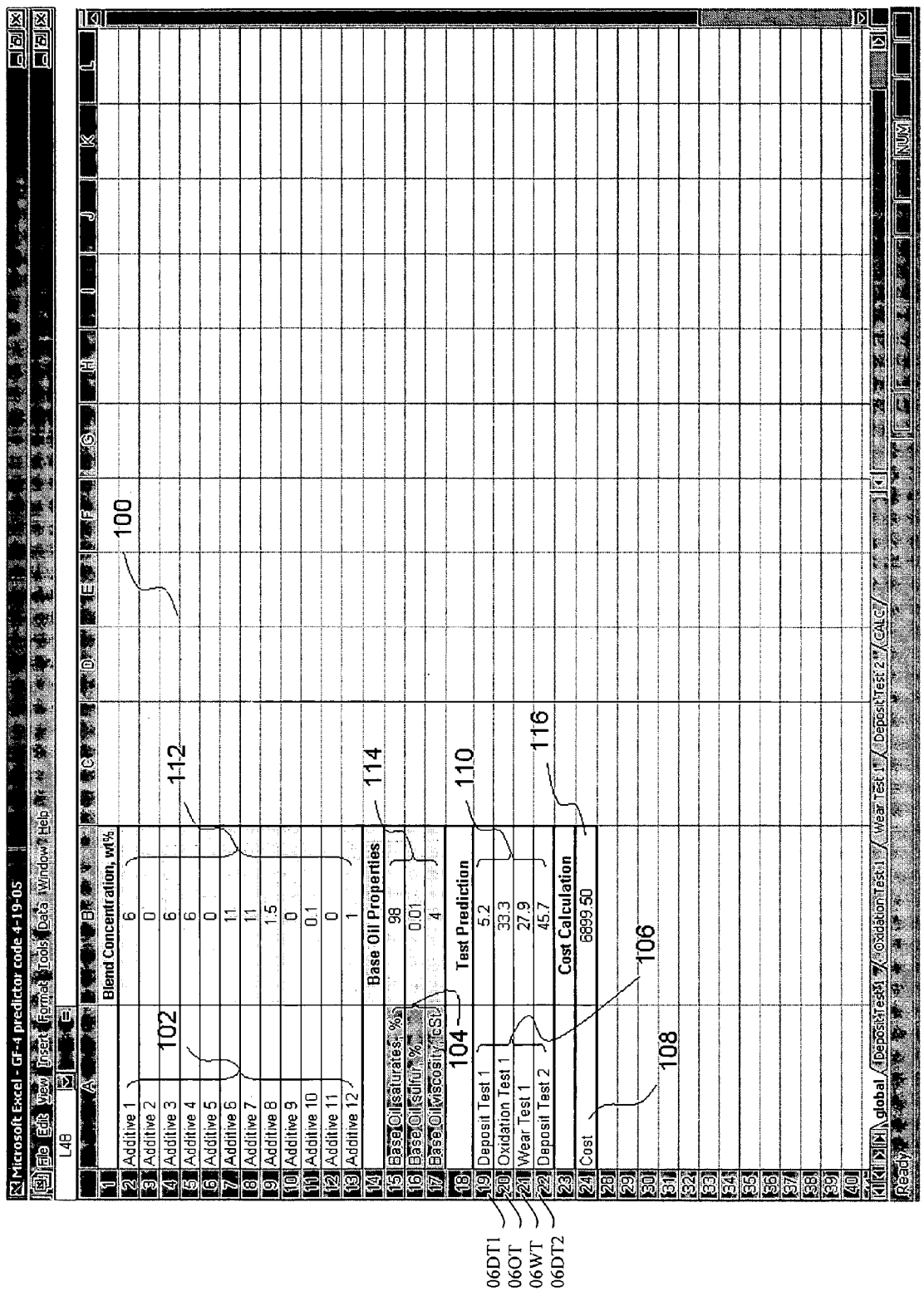
FIG. 1 is an exemplary worksheet illustrating a hypothetical lubricating oil composition and predicted test results and a calculated cost.

To illustrate the system and method of the present invention, an exemplary worksheet 100 is illustrated in FIG. 1. As shown in FIG. 1, worksheet 100 has cells which correspond to columns A through B and rows 1 through 24; the individual cells will be hereinafter referred to by column and row respectively. For example, a cell located in column A, row 1, will be referred to as cell A1. Worksheet 100 shows a hypothetical lubricating oil composition containing a lubricating oil additive package 102 having lubricating oil additives 1-12 (located in cells A2-A13, respectively), properties of a representative base oil of lubricating viscosity 104, e.g., saturate content, sulfur content, kinematic viscosity measured at 100° C. (cSt) (located in cells A15-A17, respectively), lubricating oil composition property-determining tests 106 (located in cells A19-A22, respectively) and the net average total cost (NATC) 108 for the composition (located in cell A24).

The lubricating oil composition property-determining tests 106 include, for example, a first deposit test (deposit test 1) 106DT1, an oxidation test 106OT, a wear test 106WT, and a second deposit test 106DT2. The corresponding amount 112 of each of the additives 1-12 in the lubricating oil additive package 102 and the corresponding values of the properties 114 associated with the representative base oil of lubricating viscosity 104 are set forth in cells B2-13 and cells B15-B17, respectively. As one skilled in the art would readily appreciate, the remaining amount of the lubricating oil composition (outside of the additives 1-12) can correspond to one or more base oils and the like which are present in the composition. Additionally, predicted test results calculated with reference to, for example, FIGS. 2-5, which will be described hereinbelow, are also listed in cells B19-22 in association with each test 106. If performed in a worksheet application, predicted test result 110DT1 (located in cell A13 of FIG. 2) computed from the worksheet for a lubricating oil composition property-determining test, such as that shown in FIG. 2, may be linked to the respective (cell) positions in column B of worksheet 100 (FIG. 1), and is associated with each respective test 106.

Figure 2:
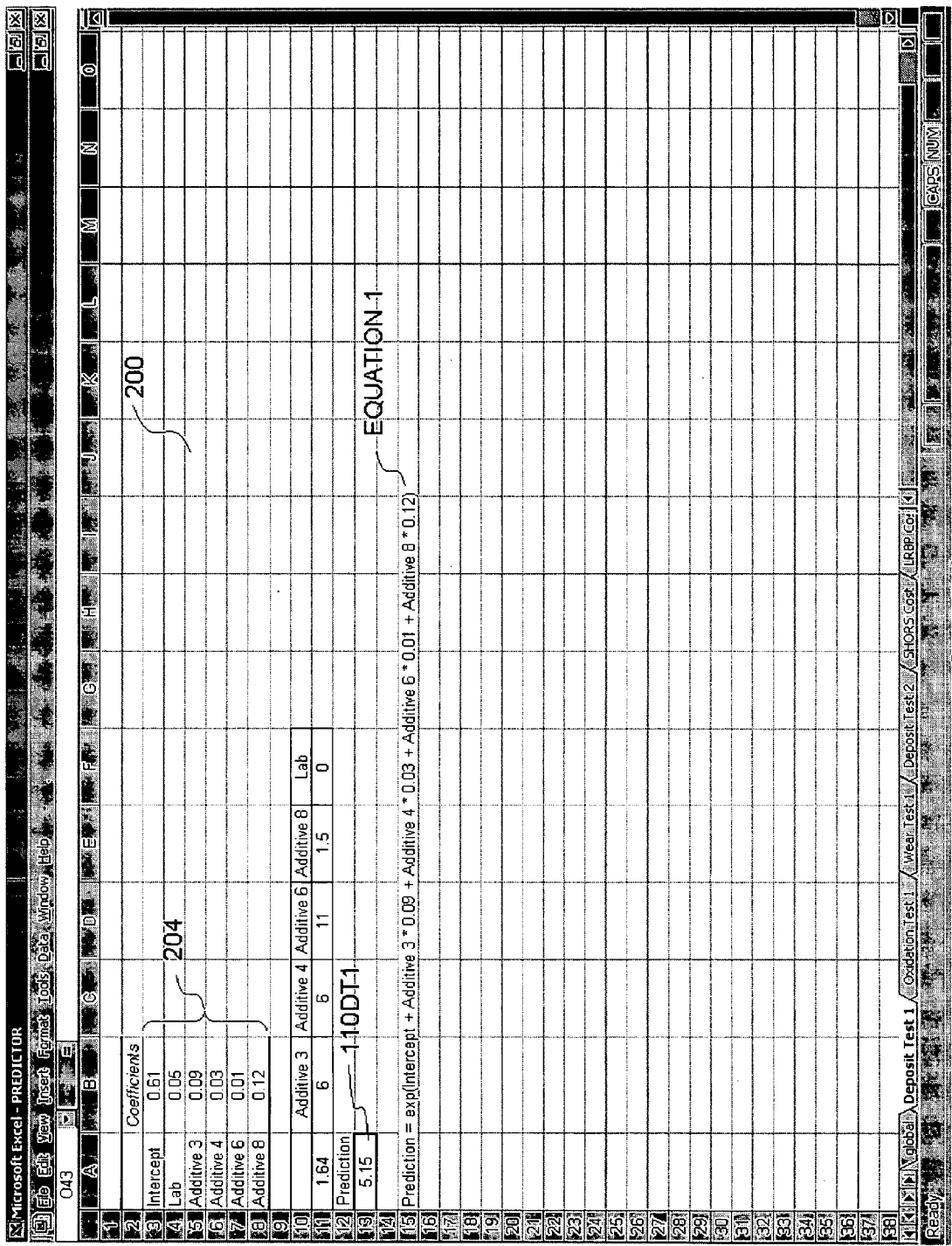
FIG. 2 is a worksheet of an exemplary linear regression model for predicting a deposit test for the hypothetical lubricating oil composition set forth in FIG. 1 according to a first deposit test result for the hypothetical lubricating oil composition set forth in FIG. 1 according to an embodiment of the present invention.

For example, the individual predicted test result 110DT1 shown in FIG. 2 corresponds to the predicted test result for the first deposit test 106DT1 shown in cell B19 of worksheet 100 (FIG. 1). Likewise, the predicted test results for other lubricating oil composition property-determining tests (e.g., the oxidation test 106OT1, the wear test 106WT1 and the second deposit test 106DT2) can be linked to the respective tests 106 as illustrated in FIG. 1. If desired, target values for the lubricating oil composition property-determining tests can be listed in cells C19-22 (FIG. 1). These targets can be any value that is required, e.g., an industry or original engine manufacturer (OEM) specification, or desired such as one from a customer so that the user can evaluate the predicted test result(s) of the hypothetical lubricating oil composition with the desired target value. Finally, the calculated cost 116 for the hypothetical lubricating oil composition is shown in cell B24 of worksheet 100 and will be described hereinbelow.

In a first step of the method of the present invention, worksheet 100 (or other quantitative arrangement) is formed containing cells for at least one lubricating oil additive 102 and at least one base oil of lubricating viscosity 104 and cells for the respective amount of each of the at least one lubricating oil additive 102 and values for the properties associated with the at least one base oil of lubricating viscosity 104. The varying amounts of the respective additive components and varying values for the properties associated with the at least one base oil of lubricating viscosity of the composition may be inputted, e.g., manually, into the respective cells associated with the at least one lubricating oil additive 102 and the at least one base oil of lubricating viscosity 104.

Generally, the lubricating oil compositions for use in the method of the present invention include a major amount of at least one base oil of lubricating viscosity, e.g., an amount of greater than 50 wt. %, preferably greater than about 70 wt. %, more preferably from about 80 to about 99 wt. % and most preferably from about 85 to about 90 wt. %, based on the total weight of the composition, and a minor amount of at least one lubricating oil additive. The expression "base oil" as used herein shall be understood to mean a base stock or blend of base stocks which is a lubricant component that is produced by a single manufacturer to the same specifications (independent of feed source or manufacturer's location) that meets the same manufacturer's specification, and that is identified by a unique formula, product identification number, or both. The base oil(s) for use herein can be any presently known or later-discovered base oil of lubricating viscosity used in formulating lubricating oil compositions for any and all applications, e.g., engine oils, marine cylinder oils, and functional fluids such as hydraulic oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C). Generally, the individual base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30, 15W-40 20W-50, SAE 30, SAE40 and the like. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fisher-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The lubricating oil additive(s) for use in the lubricating compositions can be any presently known or later-discovered additive used in formulating lubricating oil compositions. The lubricating oil additives for use herein include, but are not limited to, antioxidants, anti-wear agents, detergents such as metal detergents, rust inhibitors, dehazing agents, demulsifying agents, metal deactivators, friction modifiers, pour point depressants, antifoaming agents, co-solvents, package compatibilisers, corrosion-inhibitors, ashless dispersants, dyes, extreme pressure agents and the like and mixtures thereof. Greases will require the addition of appropriate thickeners. A variety of the additives are known and commercially available. These additives, or their analogous compounds, can be employed for the preparation of the various lubricating oil compositions herein.

Alternatively, the lubricating oil additive(s) can further contain a diluent oil to form an additive concentrate. These concentrates usually include at least from about 90 wt. % to about 10 wt. % and preferably from about 90 wt. % to about 50 wt. %, of a diluent oil and from about 10 wt. % to about 90 wt. %, preferably from about 10 wt. % to about 50 wt. %, of the foregoing additive(s). Suitable diluents for the concentrates include any inert diluent, preferably an oil of lubricating viscosity such as, for example, a base oil as described hereinbelow, so that the concentrate may be readily mixed with lubricating oils to prepare lubricating oil compositions. Suitable lubricating oils that may be used as diluents can be any oil of lubricating viscosity.

Examples of antioxidants for use as additives include, but are not limited to, aminic types, e.g., diphenylamine, phenyl-alpha-napthyl-amine, N,N-di(alkylphenyl)amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic) phenol; sulfur-containing materials, e.g., sulfurized olefins or esters and the like and mixtures thereof.

Examples of antiwear agents for use as additives include, but are not limited to, zinc dialkyldithiophosphates and zinc diaryldithiophosphates, e.g., those described in an article by Born et al. entitled "Relationship between Chemical Structure and Effectiveness of Some Metallic Dialkyl- and Diaryl-dithiophosphates in Different Lubricated Mechanisms", appearing in Lubrication Science 4-2 January 1992, see for example pages 97-100; aryl phosphates and phosphites, sulfur-containing esters, phosphosulfur compounds, metal or ash-free dithiocarbamates, xanthates, alkyl sulfides and the like and mixtures thereof.

Examples of detergents for use as additives include, but are not limited to, overbased or neutral detergents such as sulfonate detergents, e.g., those made from alkyl benzene and fuming sulfuric acid; phenates (high overbased or low overbased), high overbased phenate stearates, phenolates, salicylates, phosphonates, thiophosphonates, ionic surfactants and the like and mixtures thereof. Low overbased metal sulfonates typically have a total base number (TBN) of from about 0 to about 30 and preferably from about 10 to about 25. Low overbased metal sulfonates and neutral metal sulfonates are well known in the art.

Examples of rust inhibitors for use as additives include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers for use as additives include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$ fatty acid ester and a nitrogen-containing compound selected from the group consisting of ammonia, and an alkanolamine, e.g., those disclosed in U.S. Ser. No. 10/402,170, filed Mar. 28, 2003, the contents of which are incorporated by reference herein, and the like and mixtures thereof.

Examples of antifoaming agents for use as additives include, but are not limited to, polymers of alkyl methacrylate; polymers of dimethylsilicone and the like and mixtures thereof.

Examples of ashless dispersants for use as additives include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonoamides, thiophosphonamides and phosphoramides; thiazoles, e.g., 2,5-dimercapto-1,3,4-thiadiazoles, mercaptobenzothiazoles and derivatives thereof; triazoles, e.g., alkyltriazoles and benzotriazoles; copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof. The derivatives of these dispersants, e.g., borated dispersants such as borated succinimides, may also be used. Preferably, the dispersants are polyalkylene succinimides derived from animation of polyalkylene succinic anhydrides with polyalkylene polyamine.

If desired, prior to formulating the at least one base oil and at least one lubricating oil additive to provide the lubricating oil compositions herein, it can be advantageous to conduct molecular modeling of proposed compounds for use in the compositions (i.e., formulations) to determine which compounds may provide potential leading candidate compositions. For example, calculations can be carried out involving such factors as, for example, transition states, bond lengths, bond angles, dipole moment, hydrophobicity, etc, of the compounds. This can be carried out using known software such as, for example, Quantum Mechanics available from Accelrys (San Diego, Calif.).

Next, the lubricating oil compositions are subjected to at least one lubricating oil composition property-determining test. The term "lubricating oil composition property-determining test" as used herein shall be understood to mean a lubricating oil composition test designed to analyze a lubricating oil composition for a property or characteristic thereof when used, for example, in an internal combustion engine or as a hydraulic fluid, transmission fluid or gear oil, e.g., oxidation stability properties, antiwear properties, deposit formation properties, viscosity, and the like.

Representative examples of oxidation stability measurements include, but are not limited to, oxidation consumption data, deposit data, viscosity data, etc. Testing methods for determining such measurements are, for example, a Lube Oil Oxidator test method, a Komatsu Hot Tube test method, a thin film oxygen uptake test (TFOUT) method, e.g., ASTM D 4742), a Sequence IIIG test method, e.g., ASTM WK4452, and the like. A variety of testing machines or apparatuses are known to carry out the foregoing tests and are within the purview of one skilled in the art.

Representative examples of anti-wear property measurements, i.e., wear stability, include, but are not limited to, adhesive wear data, abrasive wear data, fatigue data and the like. Tests for determining such measurements are, for example, extreme-pressure wear tests, hydrodynamic wear tests, corrosive wear tests, a Sequence IVA, e.g., ASTM WK4485-04, a Mack T10 test method, a Cummins M11 EGR test method and the like. A variety of testing machines or apparatuses are known to carry out the foregoing tests and are within the purview of one skilled in the art. For example, Test Pin and Vee Block and Four-Ball Test assemblies, respectively, each are capable of performing the extreme pressure, hydrodynamic and corrosive wear tests either individually or in combination. An extreme-pressure wear test is associated with a situation where the lubricating oil composition has been squeezed out of, for example, an engine, leaving only a non-fluid film of anti-wear additive of the tested composition that has been chemically bonded to the interacting engine surfaces. For example, an extreme wear condition occurs between the piston ring and cylinder wall in a running internal combustion engine when the piston reaches the upper dead center and is subjected to the force of the fuel combustion explosion while the piston is, for an instant, not in sliding motion.

A hydrodynamic test is designed to test the ability of the lubricating oil compositions to prevent wear under conditions wherein a fluid lubricant film is retained between the interacting surfaces. Typically, a hydrodynamic lubricant condition occurs in an internal combustion engine between the piston rings and cylinder wall when the piston is in sliding motion during the stroke.

Finally, a corrosive wear test is designed to test the ability of the lubricating oil composition to protect the interacting surfaces from wear in a corrosive environment. The latter may be observed in an internal combustion engine due to the oxidation of components in the fuel to be combusted or in the lubricating oil composition, e.g., in the case where sulfur generates sulfuric acid.

Representative examples of deposit formation testing methods for determining deposit formation measurements include, but are not limited to, a Coking tendency test (e.g., Federal Test Method Standard 3462-791A (panel coker test method)), a Komatsu Hot Tube test method, Wolf Strip Test (e.g., DIN 51392), a Thermo-Oxidation Engine Oil Simulation Test (TEOST) MHT-4 and TEOST 33, a Sequence IIIG test method, e.g., ASTM WK4452, and the like. A variety of testing machines or apparatuses are known to carry out the foregoing tests and are within the purview of one skilled in the art.

To achieve the goals of the method of the present invention, an optimizing method (using an optimizer) for integrating the following components will be described. One or a plurality of the foregoing tests are carried out on the foregoing lubricating oil compositions to determine compliance of these compositions according to, for example, industry or OEM specifications or a customer's requirement. For example, a customer may need compliance with present industry standards, e.g., ILSAC GF-4 standards, or proposed future standards. The results of these tests are inputted and compiled in a database together with the information regarding the formulation of the lubricating oil compositions.

A mathematical calculation is then carried out on the inputted data from the lubricating oil composition property-determining tests and lubricating oil composition formulation. Examples of such mathematical calculations include, but are not limited to, linear regression analysis models, neural network analysis models, quadratic analysis models and the like. The mathematical calculations allow the user to predict any lubricating oil composition property-determining test result associated with that lubricating oil composition when hypothesizing an exemplary formulation of the same lubricating oil composition, i.e., by changing the weight amounts of the additive components 102 and optional values of the base oil properties of the base oil of lubricating viscosity 104 as shown in 112 and 114, respectively, in FIG. 1, and will be described with reference to FIG. 2.

Linear regression models, as exemplified in FIGS. 2-5, are developed from the inputted datasets of the results of the foregoing lubricating oil composition property-determining tests using at least two lubricating oil compositions. The datasets generally may contain about 2 to about 100 test results using different formulations. In theory, a linear regression model can be developed from as few as about 2 tests. For bench tests, however, the datasets are often larger and can range from about 4 to about 10,000 test results and preferably from about 4 to about 1,000 test results.

As shown in FIG. 2, a linear regression model 200 is used to determine predicted test result 110DT1 for the first deposit test 106DT1 (see FIG. 1). The coefficients 204 (including an Intercept), an optional Lab entry (i.e., laboratory site where test is being conducted), and other coefficients which correspond to Additives 3, 4, 6 and 8, respectively are derived using a linear regression equation (or other suitable equations which are well known in the art). For illustration only, an equation for deriving the predicted test result for the first deposit test 106DT1, i.e., $\text{Prediction}_{110DT1}$, is set forth below in Equation 1.

$$\text{Prediction}_{110DT1} = \exp(\text{Intercept} + \text{Additive3}*0.09 + \text{Additive4}*0.03 + \text{Additive6}*0.01 + \text{Additive8}*0.12) \quad \text{Equation (1):}$$

wherein the weight amounts of Additive 3, Additive 4, Additive 6 and Additive 8 are multiplied ("*") by their respective coefficients 204 as determined by the linear regression model. As one skilled in the art would readily appreciate, each lubricating oil additive has a particular function, e.g., an anti-wear additive or anti-oxidant additive could function to inhibit deposit formation, when used in a lubricating oil composition. Accordingly, it is dependent on the particular test being carried out to determine which additive will be used in the equation to predict the test result.

Figure 3:
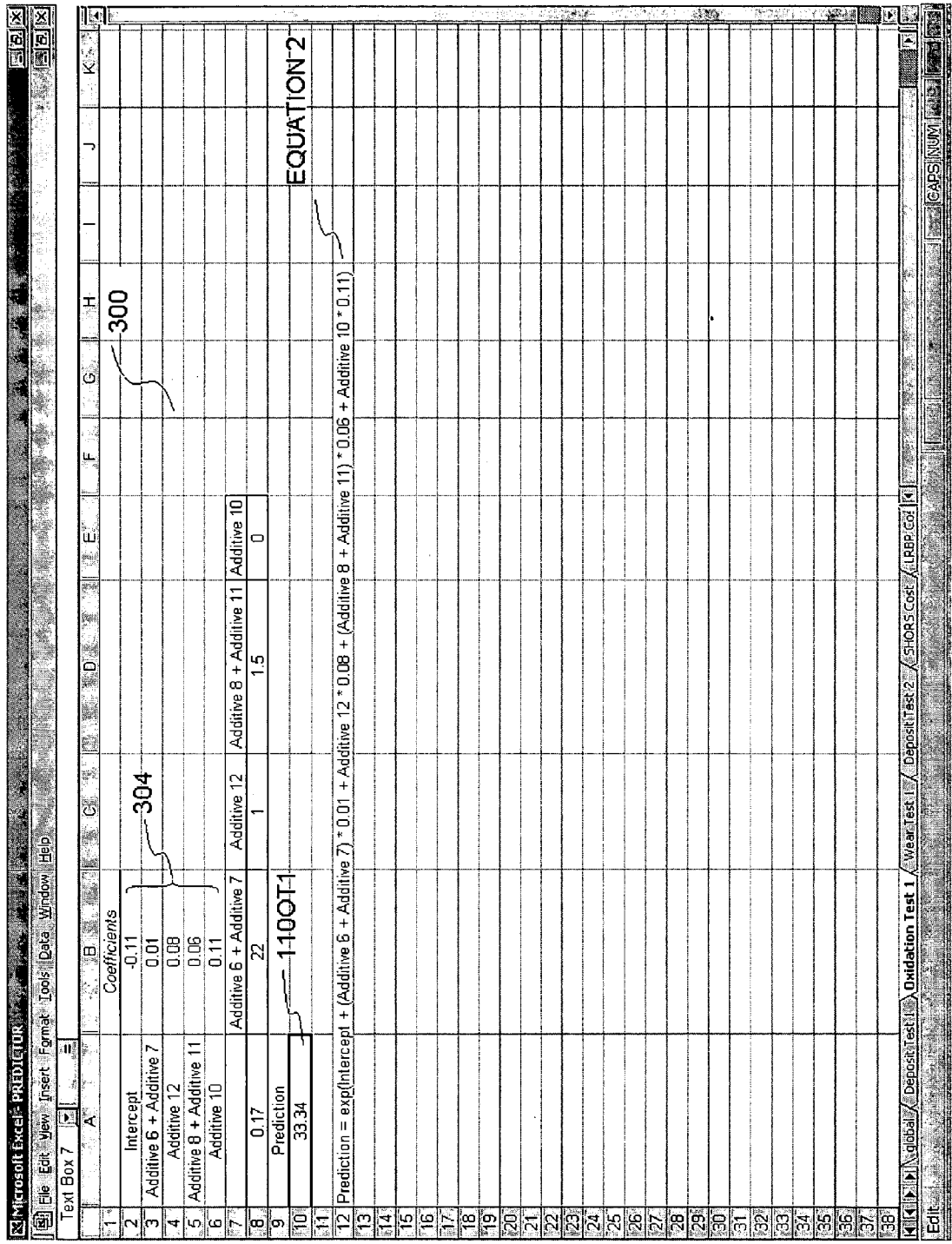
FIG. 3 is a worksheet of an exemplary linear regression model for predicting an oxidation test result for the hypothetical lubricating oil composition set forth in FIG. 1 according to an embodiment of the present invention.

As shown in FIG. 3, a linear regression model 300 is used to determine a predicted result 110OT1 for oxidation test 106OT1 (see FIG. 1). The coefficients 304 differ slightly from the coefficients shown in FIG. 2, and include an intercept, and coefficients which correspond to (Additive 6+Additive 7), Additive 12, (Additive 8+Additive 11) and Additive 10, respectively, are derived using a linear regression equation (not shown as it is well known in the art or other suitable equations which are also well known in the art) which is applied to one or more of the aforementioned datasets. For illustration only, an equation for deriving the predicted test result for the oxidation test 106OT1, i.e., $\text{Prediction}_{110OT1}$, is set forth below in Equation 2.

$$\text{Prediction}_{110OT1} = \exp(\text{Intercept} + (\text{Additive6} + \text{Additive7})*0.01 + \text{Additive12}*0.08 + (\text{Additive8} + \text{Additive11})*0.06 + \text{Additive10}*0.11) \quad \text{Equation (2):}$$

wherein the weight amounts of (Additive 6+Additive 7), Additive 12, (Additive 8+Additive 11) and Additive 10 are multiplied by their respective coefficients 304 as determined by the linear regression model. As one skilled in the art would further appreciate, when employing more than one additive which are in the same chemical family, e.g., polyalkylene succinimide family, the amount of each of these additives can be added together (e.g., additives 6 and 7) and then multiplied by their respective coefficient as determined by the linear regression model.

Figure 4:
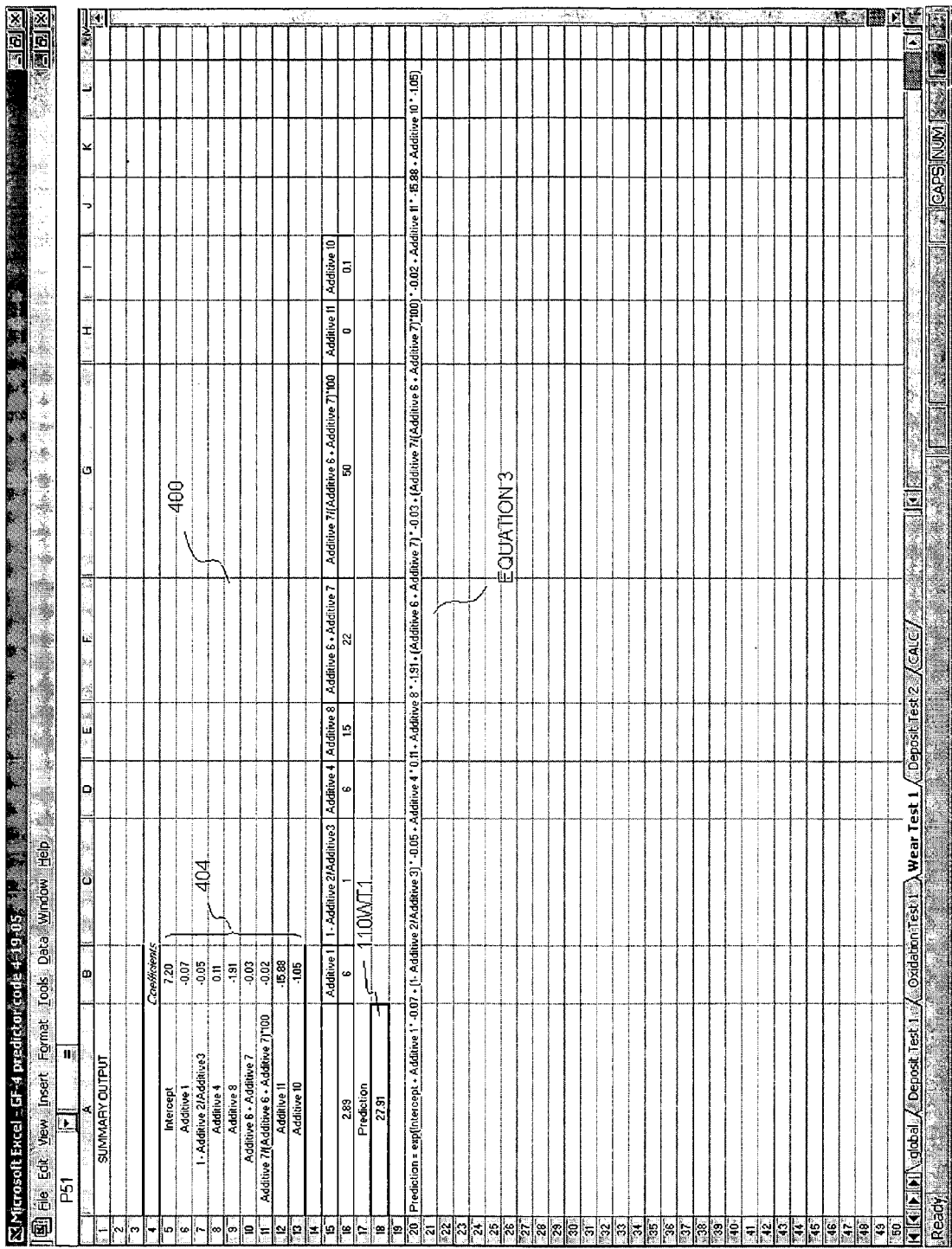
FIG. 4 is a worksheet of an exemplary linear regression model for predicting a wear test result for the hypothetical lubricating oil composition set forth in FIG. 1 according to an embodiment of the present invention.
Figure 5:
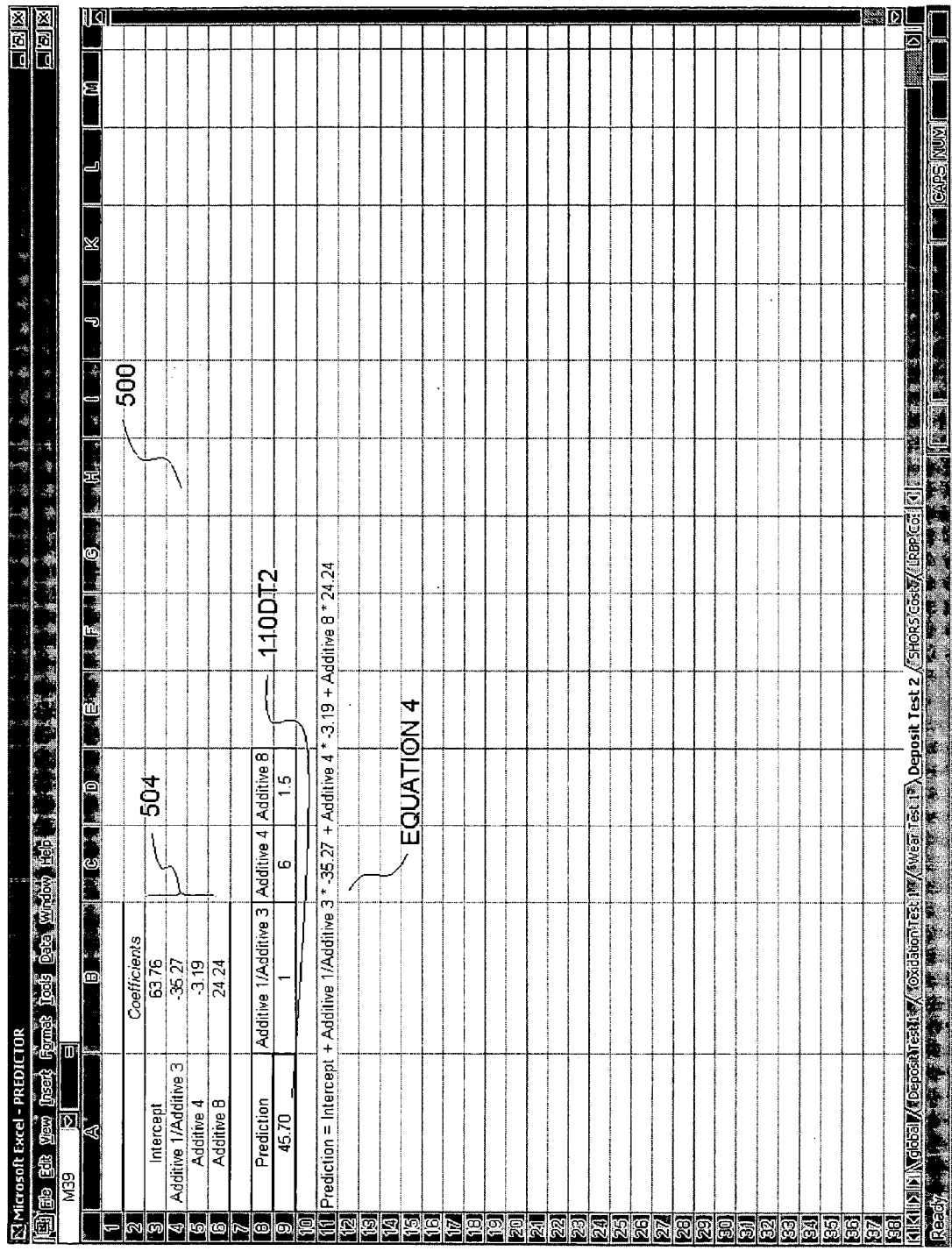
FIG. 5 is a worksheet of an exemplary linear regression model for predicting a second deposit test result for the hypothetical lubricating oil composition set forth in FIG. 1 according to an embodiment of the present invention.

FIGS. 4 and 5 similarly show linear regression models for the wear test 106WT and the second deposit test 106DT2, respectively, (which illustrate coefficients, equations and predictions which are derived in a similar fashion to the aforementioned first deposit test 106DT1 and oxidation test 106OT).

The data including the theoretical lubricating oil composition property-determining test results (from one or more tests) is optionally saved and/or displayed so that other action can be taken. In alternative embodiments, the results are reprocessed to derive yet other lubricating oil compositions using an embodiment of the present invention.

Referring now to FIG. 6, a worksheet 600 showing an exemplary cost calculation model for the lubricating oil additives employed in the hypothetical lubricating oil composition of FIG. 1 is illustrated. The lubricating oil additives 604 and their values including, for example, amount 606, cost 608 and cost contribution 610 are copied or linked to/from the global model counterparts (e.g., the corresponding components and their respective values indicated in FIG. 1). The total additive cost 602 can be copied or linked to a global model location. These results can be used for calculating the lowest cost formulation, which simultaneously meets the constraints of the performance targets for each test. To derive the best formulation, the test predictions and cost calculation are optimized, (e.g., the most desirable combination of cost and performance is selected). For example, the test predictions can be optimized by varying the additive concentrations which, in turn, can provide the minimum cost while simultaneously meeting the test performance constraints. The Solver™ program, used on most modern computer software worksheet packages, e.g., Microsoft™ Excel, Lotus 123™, Quatro Pro and the like, may be used to perform the optimization of the formulation. Moreover, these and other worksheets can offer a wide range of access to users of other programs (e.g., Microsoft™ Office Applications). Furthermore, other worksheet programs or other applications including custom-made applications can be used.

Figure 7:
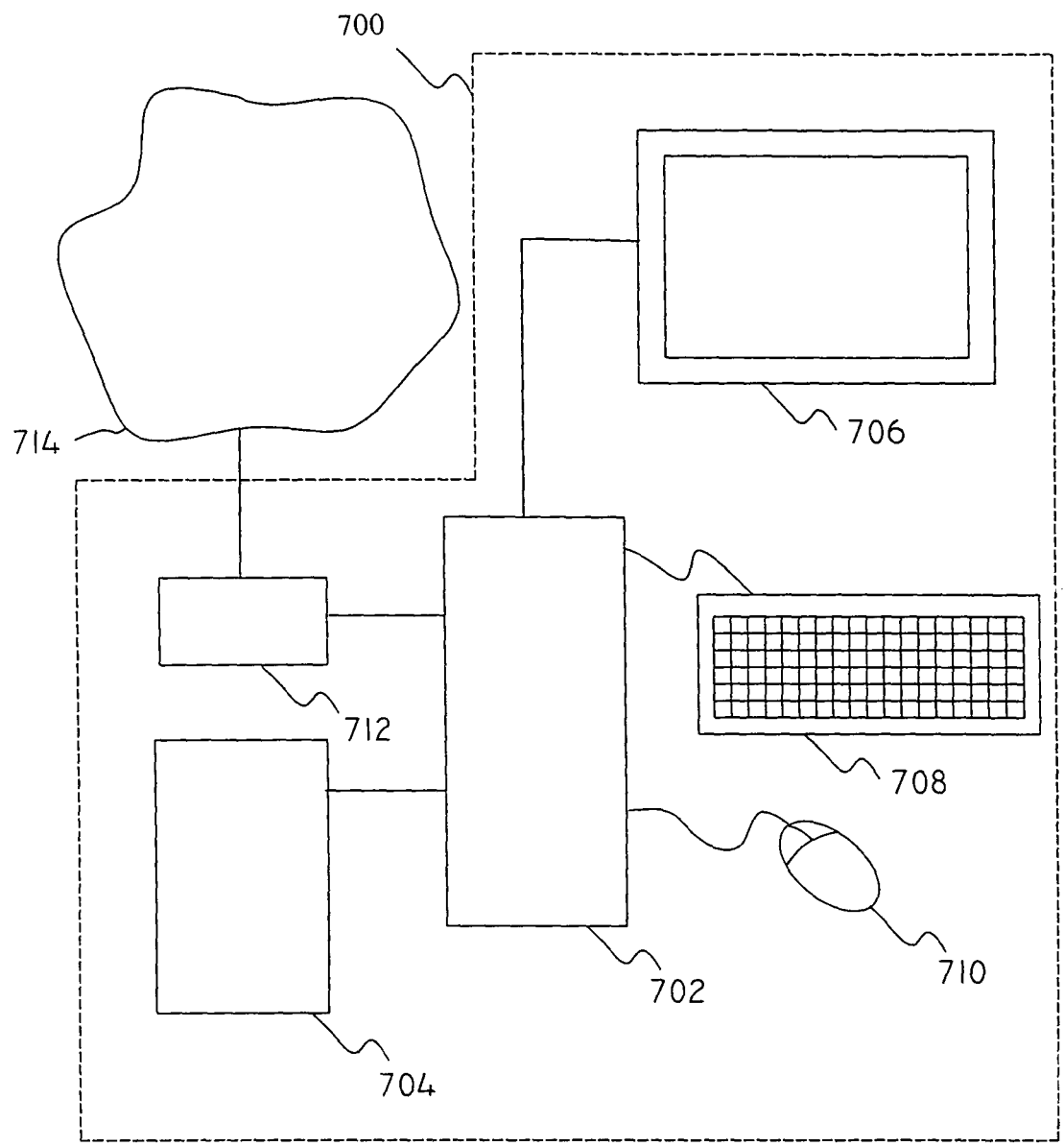
FIG. 7 is a simplified block diagram illustrating an embodiment of the present invention.

A simplified block diagram illustrating an embodiment of the present invention is shown in FIG. 7. The present invention can be realized using a system and method such as the one shown in FIG. 7. The system includes at least a personal computer 700 including a Central Processing Unit (CPU) 702, one or more memory devices 704, an I/O controller 712, a display device 706, an optional input device (e.g., keyboard) 708, an optional pointing device 710 and/or other optional input/output devices. The memory 704 can include solid state memories, one or more hard-drives and/or other storage devices including those accessed via a network connection. The CPU 702 can use any operating system which is compatible with the applications software or programs used in the present invention. The I/O controller 712 can be used by the CPU 702 to access external devices (e.g., analyzers, scanners, printers, other computers, modems, networks, etc.) 714.

The memory 704 can optionally store optional analysis tools, optimization data-bases etc. (e.g., data from the lubricating-oil-composition property-determining tests and hypothetical lubricating oil compositions as required by the specific application), which can be either directly accessed or accessed via a network.

The computer 700 generally stores and executes the application software (which, in the present embodiment is a Microsoft Excel Worksheet). The computer 700 can process and store information or can remotely access other systems which possess or can store desired data.

In another embodiment of the present invention, the CPU 702 is a standard IBM-compatible P.C. or other like device (e.g., an Apple™ computer, a PDA device, a Palm™-type device or other like device), and can include any other suitable computational device. The operating system is preferably a Microsoft (MS) Windows™ operating system but in alternative embodiments, can be any suitable operating system (e.g., MS DOS, Windows, Unix, Linux, Apple O.S., Palm O.S., etc.). The worksheet application is preferably MS Excel, but in alternative embodiments, can be any other suitable worksheet program or application.

The individual cells are accessed by using the keyboard 708, the mouse 710 or other like device to select cells and input variables. The keyboard 708, mouse 710 or other suitable device can also be used to select various features of the application (e.g., select graphs, print, etc.) and can also be used to control the initiation, and termination of the application program in additional to other known uses.

The method of the present invention combines the data models, cost calculation, and optimization routines into an integrated system allowing optimized formulations of lubricating oil compositions to be mathematically derived, in contrast to existing approaches that rely on the experience and intuition of a human formulator. The integration of these processes allows the formulation to be optimized for lowest cost as well meeting the constraints of test pass/fail limits. Accordingly, the method and system of the present invention advantageously decreases the time and effort required to formulate and optimized lubricating oil compositions, and eliminates human error.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A computer system for screening a lubricating oil composition having at least one base oil of lubricating viscosity and at least one lubricating oil additive, the system comprising:
    (a) means for inputting a desired type and amount of each of the at least one lubricating oil additive, based on the total weight of the lubricating oil composition and, optionally, a value of at least one property associated with each of the at least one base oil of lubricating viscosity;
    (b) means for computing a prediction of at least one lubricating-oil-composition property-determining test result for the lubricating oil composition; and
    (c) means for computing a cost for the lubricating oil composition.

2. The system of claim 1, wherein the system generates at least one test result which comprise fields of information comprising at least one of deposit formation properties, anti-wear properties and oxidation properties.

3. The system of claim 1, wherein the at least one base oil of lubricating viscosity is a natural or synthetic oil.

4. The system of claim 1, wherein the at least one lubricating oil additive is selected from the group consisting of anti-oxidants, anti-wear agents, detergents, rust inhibitors, dehazing agents, demulsifying agents, metal deactivating agents, friction modifiers, pour point depressants, antifoaming agents, co-solvents, package compatibilizers, corrosion-inhibitors, ashless dispersants, dyes, extreme pressure agents and mixtures thereof.

5. The system of claim 1, wherein the means for computing a prediction of at least one lubricating oil composition property-determining test result, for the lubricating oil composition uses one of a linear regression calculation, a neural network calculation and a quadratic calculation.

6. The system of claim 1, wherein the means for computing a prediction of at least one lubricating-oil-composition property determining test uses a mathematical calculation model wherein coefficients in each mathematical calculation model are used to build equations for predicting each of the at least one test result for hypothetical formulations.

7. The system of claim 1, wherein the means for computing a prediction of at least one lubricating-oil-composition property-determining test result for the lubricating oil composition uses a linear regression model having coefficients which are used to build equations for predicting test results for hypothetical formulations of lubricating oil compositions having at least one base oil of lubricating viscosity and at least one lubricating oil additive.

8. The system of claim 1, further comprising (d) means for conducting an optimization routine to derive the lowest cost for a lubricating oil composition, which simultaneously meets given constraints of a performance targets for each test.

9. A computer program device readable by a machine, tangibly embodying a program of instructions executable by the machine to perform method steps for screening a lubricating oil composition having at least one base oil of lubricating viscosity and at least one lubricating oil additive, the method steps comprising:
  (a) inputting into a computational device an amount of each of the at least one lubricating oil additive, based on the total weight of the lubricating oil composition and, optionally, a value of at least one property associated with each of the at least one base oil of lubricating viscosity;
  (b) computing a prediction of at least one lubricating oil composition property-determining test result for the lubricating oil composition; and
  (c) computing a cost for the lubricating oil composition.

10. The computer program device of claim 9, wherein the step of computing a prediction of at least one lubricating oil composition property-determining test is done to determine compliance to a target specification.

11. The computer program device of claim 9, wherein the step of computing a prediction of at least one lubricating oil composition property-determining test result comprises fields of information including at least one of deposit formation properties, anti-wear properties and oxidation properties.

12. The computer program device of claim 9, wherein the at least one base oil of lubricating viscosity is a natural or synthetic oil.

13. The computer program device of claim 9, wherein the at least one lubricating oil additive is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

14. The computer program device of claim 9, wherein the step of computing a prediction of at least one lubricating oil composition property-determining test result uses one of a linear regression calculation, a neural network calculation or a quadratic calculation.

15. The computer program device of claim 9, wherein the step of computing a prediction of at least one lubricating-oil-composition property-determining test result for the lubricating oil composition uses a linear regression model having coefficients which are used to build equations for predicting test results for hypothetical formulations of lubricating oil compositions having at least one base oil of lubricating viscosity and at least one lubricating oil additive.

16. The computer program device of claim 9, further comprising (d) conducting an optimization routine to derive the lowest cost for a lubricating oil composition, which simultaneously meets given constraints of a performance targets for each test.

\* \* \* \* \*